US008009139B2

(12) United States Patent
Lurz et al.

(10) Patent No.: US 8,009,139 B2
(45) Date of Patent: Aug. 30, 2011

(54) LABORATORY APPARATUS WITH A CONTROL DEVICE

(75) Inventors: Werner Lurz, Kaltenkirchen (DE); Wolfram Meyer, Hamburg (DE); Roland Kleindienst, Borsdorf (DE); Heiko Muller, Panitzsch (DE)

(73) Assignee: Eppendorf AG, Hamburg (DE)

( * ) Notice: Subject to any disclaimer, the term of this patent is extended or adjusted under 35 U.S.C. 154(b) by 753 days.

(21) Appl. No.: 11/600,532

(22) Filed: Nov. 16, 2006

(65) Prior Publication Data

US 2007/0132723 A1 Jun. 14, 2007

(30) Foreign Application Priority Data

Dec. 13, 2005 (DE) .................. 20 2005 019 472 U

(51) Int. Cl.
*G09G 5/00* (2006.01)
*H01H 3/00* (2006.01)
*G06F 3/02* (2006.01)
*G06F 3/033* (2006.01)
*H01H 13/70* (2006.01)
*H01H 19/00* (2006.01)
*H01H 19/14* (2006.01)

(52) U.S. Cl. ........ 345/156; 307/139; 345/168; 345/184; 200/5 R; 200/11 R; 200/564

(58) Field of Classification Search .......... 345/156–158, 345/168–169, 173, 184; 340/679–680; 399/100; 700/17, 180; 701/33; 307/112, 139–140; 200/5 A, 5 R, 11 R, 11 TW, 564; 463/37–38

See application file for complete search history.

(56) References Cited

U.S. PATENT DOCUMENTS

| | | | | |
|---|---|---|---|---|
| 5,283,862 | A * | 2/1994 | Lund | 345/173 |
| 5,438,331 | A * | 8/1995 | Gilligan et al. | 341/35 |
| 5,615,083 | A * | 3/1997 | Burnett | 361/679.1 |
| 6,009,363 | A * | 12/1999 | Beckert et al. | 701/33 |
| 6,366,747 | B1 * | 4/2002 | Roller | 399/110 |
| 6,750,407 | B2 * | 6/2004 | Song et al. | 200/5 A |
| 6,879,262 | B1 * | 4/2005 | Todteberg et al. | 340/679 |
| 2003/0033026 | A1 * | 2/2003 | Murphy | 700/9 |

* cited by examiner

*Primary Examiner* — Lun-Yi Lao
*Assistant Examiner* — Jarurat Suteerawongsa
(74) *Attorney, Agent, or Firm* — Vidas, Arrett & Steinkraus

(57) ABSTRACT

A laboratory apparatus having at least one control device (4) comprising an electric printed-circuit board (15) of the control device (4) that is disposed on an instrument body (2) of the laboratory apparatus (1) and has at least one electric control element (16, 18), at least one operator interface (6) of the control device (4) including at least one operator control (11, 33); a retaining device (29, 30) for detachably holding the operator interface (6) on the instrument body (2) with the operator control (11, 33) oriented to the control element (16, 18), and a mechanical and/or magnetic connection for detachably joining the control element (16, 18) mechanically and/or magnetically to the operator control (11, 33).

19 Claims, 4 Drawing Sheets

LABORATORY APPARATUS WITH A CONTROL DEVICE

CROSS-REFERENCE TO RELATED APPLICATIONS

Not applicable.

STATEMENT REGARDING FEDERALLY SPONSORED RESEARCH

Not applicable.

BACKGROUND OF THE INVENTION

Inventive laboratory apparatus specifically are laboratory centrifuges, thermomixers, and other sample preparation apparatus. They have control devices which make it possible to set the laboratory apparatus working and stop them working and adjust the operating conditions as required. For example, the control device of a laboratory centrifuge allows for one or more of the functions below: turn the apparatus on and off, open the centrifuge lid, start and stop the centrifugation procedure, adjust the number of revolutions and centrifugation time, select a centrifugation short-time mode, and adjust the centrifugation temperature.

The control device is a keyboard with press keys, for example. It is frequently designed as a touch-sensitive membrane keyboard. Control devices with rotary knobs for adjusting the speed and centrifugation time are also known. Control devices which have a keyboard and rotary knobs are known as well.

Users of laboratory apparatus sometimes prefer control devices which have keys only, specifically control devices with touch-sensitive membrane keyboards. Membrane keyboards are liquid-tight and make it easier to clean the control device. Other users prefer control devices in which at least some of the control elements have rotary knobs. Rotary knobs make it easier to rapidly set an operating parameter within a wide range. Moreover, they are preferred by female persons carrying long fingernails.

Known laboratory apparatus do not come up to the different needs because they are only available with one type of control device each so that they exclusively present push-button switches, exclusively present rotary knobs or have push-button switches in combination with rotary knobs. It would involve too much effort to produce laboratory apparatus of the same type with different control devices in order to allow the user a choice in acquiring a laboratory apparatus. Furthermore, this would not come up to application cases where a laboratory apparatus is shared amongst users who prefer different types of the control device.

Accordingly, it is the object of the invention to provide an easy-to-use laboratory apparatus with an control device.

BRIEF SUMMARY OF THE INVENTION

The inventive laboratory apparatus having at least one control device comprises: an electric printed-circuit board of the control device that is disposed on an instrument body of the laboratory apparatus and has at least one electric control element, at least one operator interface of the control device including at least one operator control, a retaining device for detachably holding the operator interface on the instrument body with the operator control oriented to the control element, and a mechanical and/or magnetic connection for detachably joining the control element mechanically and/or magnetically to the operator control.

The inventive laboratory apparatus comprises: at least one control device with at least one electric control element and at least one operator control connected thereto; a retaining device for detachably holding the control device on an instrument body of the laboratory apparatus, and an electric connection for detachably joining the control device, which is held on the instrument body, electrically to the instrument body.

In the first solution variant, the operator interface is adapted to be detachably mounted on the instrument body by means of the retaining device. To this end, at least one operator control of the operator interface is detachably coupled to a control element of an apparatus-sided printed-circuit board via a mechanical and/or magnetic (e.g. electromagnetic or permanently magnetic) connection. Thus, the operator interface is detachably connected to the instrument body via a via a mechanical and/or magnetic (e.g. electromagnetic or permanently magnetic) interface. In the second solution variant, the control device as a whole is adapted to be detachably connected to the instrument body by means of the retaining device. At this point, an electric connection is established between the control device and the instrument body in order to connect any electric control element of the control device electrically to an electric control within the instrument body. Thus, the control device is adapted to be detachably connected to the instrument body via a mechanical and electrical interface.

Thus, it is for the first time that laboratory apparatus having an operator interface or control device are provided which can be detached from the instrument body easily and rapidly. As a result, the laboratory apparatus may be readily equipped with an operator interface or control device which meets the respective user's demands.

Inventive laboratory apparatus may be fitted and delivered with various operator interfaces or control devices from the very beginning so that the user can make a selection already during their acquisition. Users who want to modify an operator interface or control device following the purchase of a laboratory apparatus may exchange them with or purchase them additionally from the manufacturer or retailer. Likewise, it is possible to deliver the laboratory apparatus with a plurality of operator interfaces or control devices from the very beginning so that the user may install an operator interface or control devices of his choice on the laboratory apparatus. Various users of the same laboratory apparatus may install that operator interface or control device which is to their liking on the laboratory apparatus easily and rapidly.

Hence, the invention makes it possible to exchange operator interfaces and control devices in a non-complicated, safe, and rapid manner so that the user obtains the laboratory apparatus with the design type he prefers for the control elements. Moreover, it allows to replace damaged operator interfaces or control devices easily and rapidly with no need to repair the laboratory apparatus as a whole.

Preferred aspects of the invention variants are indicated in the dependent claims.

As mentioned before, the laboratory apparatus may be delivered with a single operator interface or control device. In case of need, the user may be supplied with a different operator interface or control device later on, possibly in exchange for the operator interface or control device which was delivered along with the laboratory apparatus originally. According to an aspect, the laboratory apparatus comprises a plurality of operator interfaces or control devices with at least one operator control of different types for exchangeably holding a selected operator interface or control device on the instrument body of the laboratory apparatus by means of the retaining device. In other words, the laboratory apparatus is delivered with various operator interfaces or control devices straight away so that the respective users are able to install the operator interface or control device preferred by them on the laboratory apparatus.

The control device may be fitted with various operator controls, e.g. rocker switches or sensor keys. According to an aspect, at least one operator control is a press key and/or rotary knob. Press keys, specifically as membrane keys, are preferred in many cases on laboratory apparatus, particularly because they are safe in operation and can be cleaned readily under laboratory conditions. Rotary knobs are frequently preferred, particularly because they allow for a rapid adjustment of variable operating values.

According to another aspect, various operator interfaces or control devices differ from each other in that at least one rotary knob is present in place of at least one push-button key, or vice versa. This allows the user to select various operator interfaces or control devices having press keys or rotary knobs.

According to another aspect, at least one control device has a substantially flat operator interface with at least one push-button key. This is beneficial, in particular, for preventing dirt coatings and for cleaning. According to a preferred aspect, the control device has a touch-sensitive membrane keyboard. Touch-sensitive membrane keyboards are liquid-tight so that they also function even when wetted by liquids, and are wipe-clean. These advantages may be provided for some portion of the control device which is configured as a touch-sensitive membrane keyboard while some other portion may be configured in another way. According to a preferred aspect, all of the operator controls of the control device are touch-sensitive membrane keys so that all of the operator controls are liquid-tight.

According to an aspect of the touch-sensitive membrane keyboards, the operator interface has at least one flexible interfacial element which, when the operator interface is held on the instrument body, has an inside abutted directly, or via an adapter button indirectly, to the front face of a press key disposed on the printed-circuit board. Thus, the flexible interfacial element acts onto the press key directly, or via the adapter button. Pressing the flexible interfacial element causes an actuation of the press key. The contact with the press key is cancelled when the operator interface is detached from the instrument body. The design combines a touch-sensitive membrane keyboard with the operator interface exchangeably disposed on the instrument body.

The adapter button allows to put the push-button switch out of function if the operator interface is exchanged against an operator interface which has no adapter button so that the push-button switch cannot be actuated by pressing the operator interface. In contrast, the operator interface installed in exchange may exhibit a rotary knob, for example.

According to an aspect, the operator interface has a rigid operator interface bottom portion with at least one hole partially accommodating the front face of a push-button switch or adapter button and a membrane disposed at the outside of the interface bottom portion. The membrane forms the flexible interfacial element above the hole. This structure of the operator interface with a touch-sensitive membrane keyboard is particularly simple.

According to another aspect, at least one adapter button which plunges into a hole of the operator interface bottom portion and into a hole of the perforated mask and has a circumferentially-sided protrusion is arranged to be axially slidable between the operator interface bottom portion and at least one perforated mask attached to the operator interface bottom portion. The adapter button plunges into a hole of the operator interface bottom portion, on one hand, and into a hole of the perforated mask, on the other. The adapter button is captively held by the edge protrusion, which preferably is a circumferential disc-shaped edge, between the perforated mask and the operator interface bottom portion. As a result, the adapter button is captively joined to the operator interface so that the operator interface, along with the adapter button, may be dismounted from the instrument body. This also facilitates the assembly of the operator interface to the instrument body.

According to an aspect, at least one operator interface has at least one rotary knob at the outside, an axis of rotation joined to the rotary knob and penetrating through the operator interface, an angle encoder which is joined to the axis of rotation and is disposed on the printed-circuit board, and a detachable connection fixed for rotation between the rotary knob and the angle encoder. This helps achieve a constructionally easy, detachable mechanical connection between a rotary knob and an angle encoder.

According to another aspect, at least one axis of rotation penetrating through a hole of the perforated mask and having an annular disk at the circumference is disposed between the operator interface bottom portion and at least one perforated mask attached to the operator interface bottom portion. The annular disc secures the axis of rotation to the operator interface so that it is adapted to be mounted on and dismounted from the instrument body. On one hand, the axis of rotation is joined to a rotary knob through a hole of the operator interface bottom portion where the axis of rotation be led to the outside through the hole or the rotary knob can engage the hole. On the other hand, the axis of rotation can be detachably joined to the angle encoder in order to be fixed for rotation through the hole of the perforated mask. For example, the axis of rotation has a snap-fit connection fixed for rotation with the angle encoder. For this purpose, for example, the axis of rotation externally has one or more flattened portions which bear on corresponding flattened portions of a seat of the angle encoder when the axis of rotation has been introduced into the angle encoder, or vice versa.

According to an aspect, a display of a display device is visible in a window of the control device. For example, the display visualizes the operating condition and possibly settings of the laboratory apparatus to the user.

According to another aspect, the printed-circuit board carries a display device and the operator interface has the window. Thus, the display device is disposed on the instrument body permanently and the display is visible through the window of the respective operator interface installed on the instrument body.

The printed-circuit board of the control device is integrated in a seat of the instrument body, for example, so that there is no need for a particular casing of the control device. According to an aspect, the control device has a casing bottom portion held on the instrument body in which the printed-circuit board is retained and which exhibits the retaining device for detachably hold the operator interface on the casing bottom portion. In this design type, the control device has a casing of its own which is defined by the casing bottom portion and the operator interface. This casing may be joined to the instrument body fixedly or detachably again or may be held thereon. This also allows for an easy exchange of the entire control device if the printed-circuit board is to be exchanged as well, for example.

Further, this aspect allows for a flexible arrangement of the control device on the instrument body in order to enable an optimum setting for the user. According to an aspect, a pivoting bracket for pivotably holding the casing bottom portion on the instrument body exists between the casing bottom portion and the instrument body. According to another aspect, a detenting device for the casing bottom portion in different pivoting positions with respect to the instrument body exists between the casing bottom portion and the instrument body.

The object is attained, according to the third solution variant, by a control device having the features of claim 20 which can also present the features of one of the preceding claims.

The inventive laboratory apparatus with a control device comprises: at least a pair of keys one key of which serves for increasing a setting and the other key serving for decreasing the same setting, and at least on angle encoder with a detachable rotary knob for adjusting the same setting.

In this solution variant, the rotary knob or the keys can be utilized to adjust the setting. If the rotary knob is preferred it is left and utilized on the control device. The key function may be switched off, if desired. Likewise, it is possible for the rotary knob to conceal the keys so as to make them inoperable when the rotary knob is arranged on the control device. If keys are preferred the rotary knob is separated from the control device. It will then exclusively be the keys which are available for the operation of the laboratory apparatus. According to an aspect, the control device has further operator controls, e.g. several keys and/or rotary knobs.

According to an aspect, the rotary knob has a releasably mechanical and/or magnetic connection to the angle encoder. According to an aspect, the magnetic connection penetrates through a closed operator interface so that the liquid tightness of the control device can be ensured. A simple rotary support is achieved here, for example, by snap-fitting the rotary knob onto an axis protruding from the operator interface. According to an aspect, the rotary knob or an axis connected thereto at least partially penetrates through a hole in an operator interface, and is connected to the angle encoder mechanically or a stopper is adapted to be forced into the hole when the rotary knob is detached from the angle encoder. Thus, the hole needed for a mechanical connection of the rotary knob and angle encoder is closed to be liquid-tight after the rotary knob is removed.

According to an aspect, there is a locking device which prevents the operator interface or control device or rotary knob from getting off the laboratory apparatus or the rotary knob from getting off the angle encoder when the centrifuge is turned on or executes certain functions. The locking device is active, for example, when the centrifuge carries out centrifugation. This ensures, specifically for safety reasons, that the centrifuge is operable when working in the centrifuging mode. When in operation, however, the locking device may also prevent any access from being obtained to live elements, e.g. a printed-circuit board.

The locking device can operate mechanically and/or electrically and in any other possible mode. For example, it has a locking bar which can be displaced by an electric actuator which is controlled by an electric control of the laboratory apparatus and locks or unlocks the control device or rotary knob. In a mechanical design, mechanical locking elements are brought to a position locking the operator interface or control device or rotary knob if certain operator controls are actuated or the rotor drive is running.

According to an aspect, the laboratory apparatus is a laboratory centrifuge or sample preparation apparatus. The sample preparation apparatus is a thermomixer, for example.

BRIEF DESCRIPTION OF THE SEVERAL VIEWS OF THE DRAWINGS

The invention will be described in more detail below with reference to the accompanying drawings of an embodiment. In the drawings.

DETAILED DESCRIPTION OF THE INVENTION

While this invention may be embodied in many different forms, there are described in detail herein a specific preferred embodiment of the invention. This description is an exemplification of the principles of the invention and is not intended to limit the invention to the particular embodiment illustrated.

Figure 1:
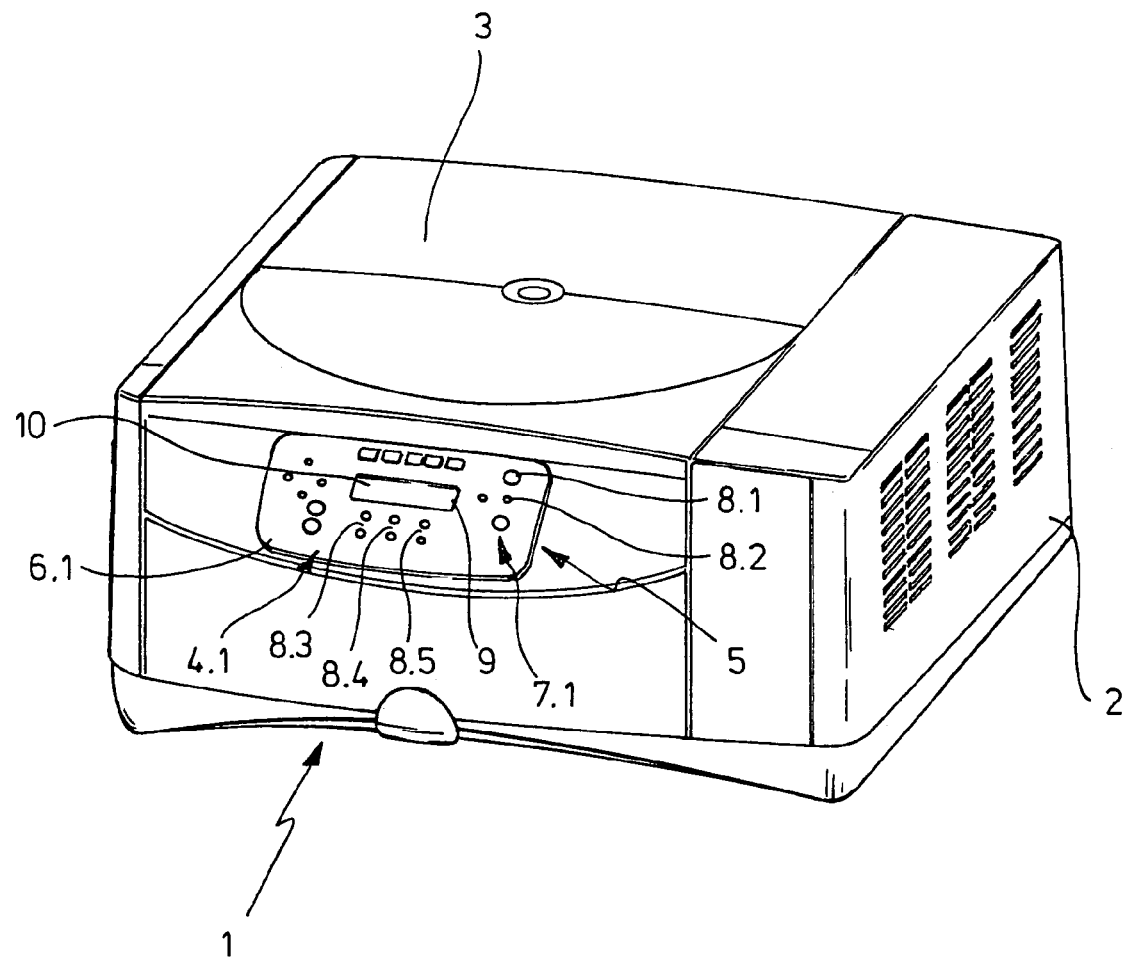
FIG. 1 is a laboratory centrifuge having a control device with an operator interface solely comprising keys in an oblique perspective view from top.

In FIG. 1, a laboratory centrifuge 1 has an instrument body 2 in which a centrifuge rotor, a rotor drive, and an electric control are disposed, but cannot be seen in the drawing. At top, the instrument body 2 has a casing lid 3 which can be lifted up about a hinge at a rear edge in order to allow for an access to the centrifuge rotor. After the casing lid 3 is lifted up it becomes possible to place receptacles with samples requiring centrifugation in the rotor or remove the receptacles therefrom.

The instrument body 2, on a front side wall, has a control device 4.1 which exhibits a casing bottom portion 5 and an operator interface 6.1.

The operator interface 6.1 comprises keys of a touch-sensitive membrane keyboard 7.1. In particular, there are keys 8.1 for turning the instrument on and off, 8.2 for starting and stopping the centrifuge, and pairs of keys 8.3 for increasing and decreasing the centrifugation time, 8.4 for increasing and decreasing the centrifugation temperature, and 8.5 for increasing and decreasing the rotor speed.

The operator interface 6.1 has mounted therein a window 9 through which a display 10 can be seen.

Figure 2:
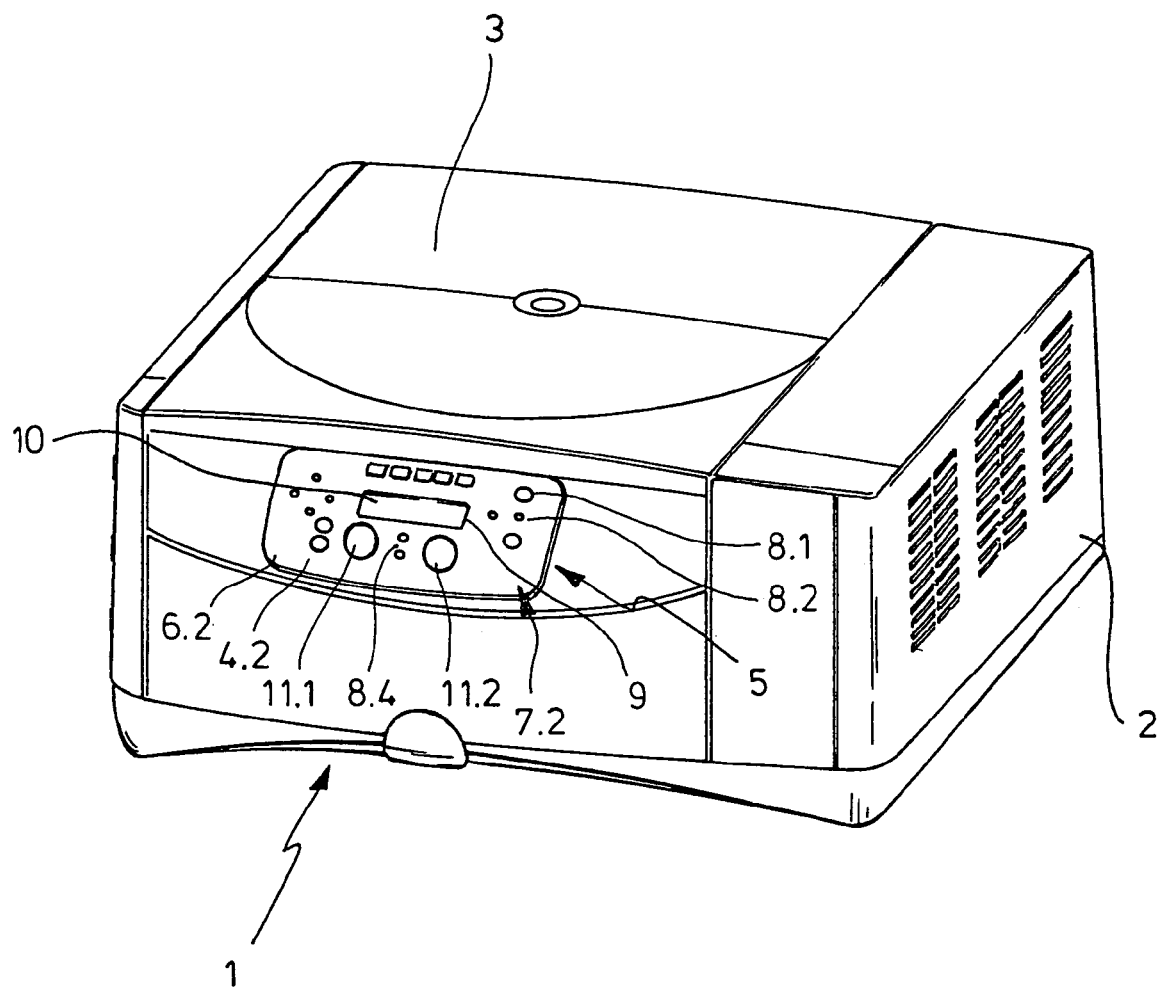
FIG. 2 the same laboratory centrifuge with an operator interface comprising keys and rotary knobs in the same perspective view.

In FIG. 2, the centrifuge 1 has a control device 4.2 with the same bottom portion 5 and another operator interface 6.2, which has a rotary knob 11.1 for increasing and decreasing the centrifugation time in place of the pair of keys 8.3, and has a rotary knob 11.2 for increasing and decreasing the rotor speed instead of the pair of keys 8.5. For the rest, the operator interface 6.2 has a touch-sensitive membrane keyboard 7.2 and a window 9 which coincide with the touch-sensitive membrane keyboard 7.1.

Figure 3:
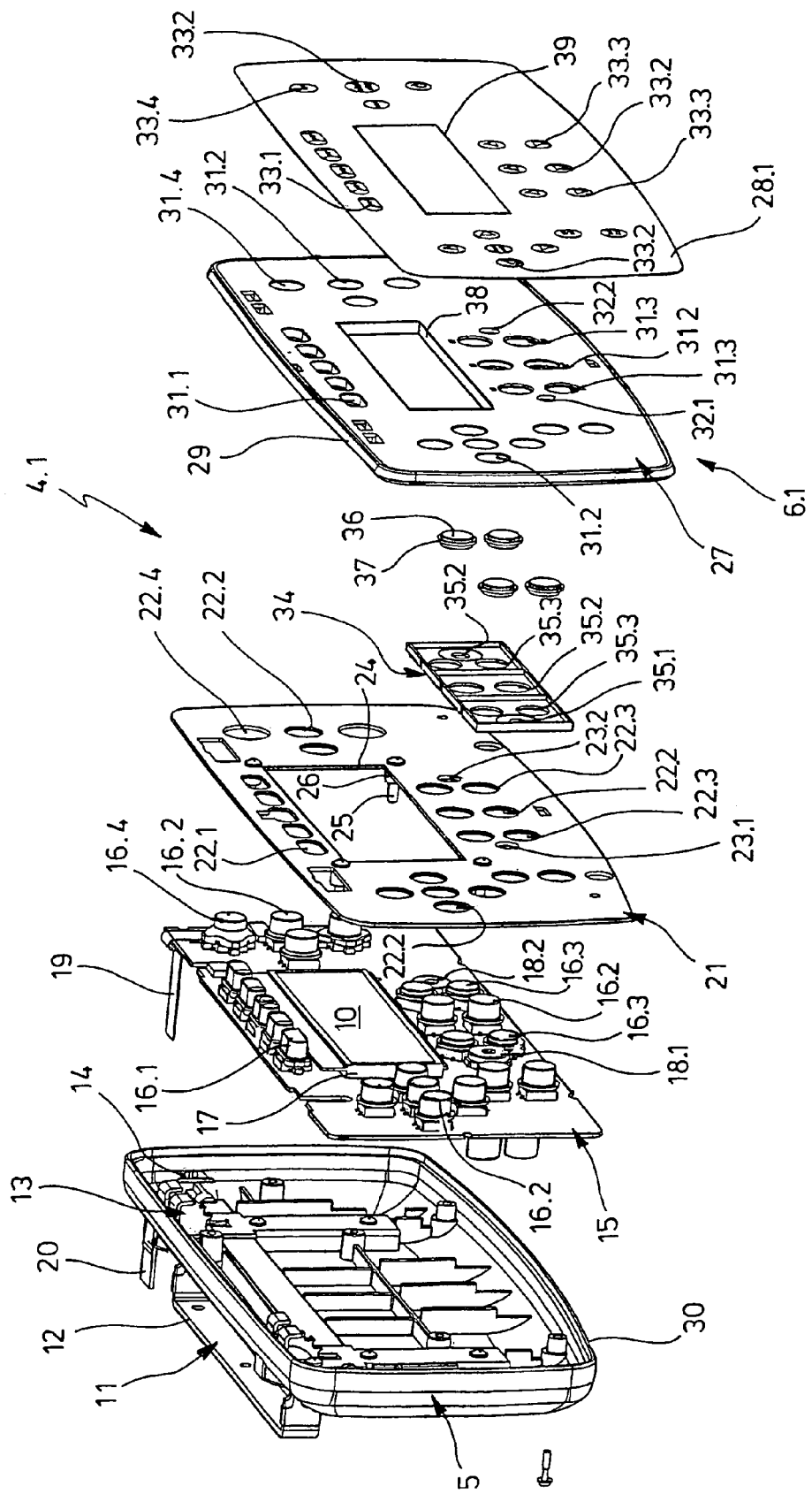
FIG. 3 the control device of the laboratory centrifuge with an operator interface solely comprising keys in an exploded perspective view.

In FIG. 3, the shell-shaped bottom casing portion 5 has a pivoting holder 11 with a bracket 12 for attaching it to the instrument body 2. The pivoting holder 11 has associated therewith a detenting device 13 for the bottom casing portion 5 at various pivoting positions and an unlocking button 14 for unlocking the detenting device 13.

A multiplicity of push-button switches of different types 16.1, 16.2, 16.3, 16.4 are disposed on the printed-circuit board 15. Further, the printed-circuit board 15 carries a display device 17 with the display 10. Moreover, angle encoders 18.1, 18.2 are disposed on the printed-circuit board.

An electric connection cable 19 is led away from the printed-circuit board 15.

The printed-circuit board 15 is adapted to be placed on posts or webs of the bottom casing portion 5 and to be bolted thereto. An insulated electric connection cable 20 is led out of the rear of the bottom casing portion 5.

A front panel 21 is adapted to be bolted onto the printed-circuit board 15. The panel has holes 22.1, 22.2, 22.3, 22.4 for the various push-button switches 16.1 to 16.4 into which those plunge with their push-buttons or which are penetrated through by the push-buttons. Further, the front panel 21 has holes 23.1, 23.2 which are oriented towards the angle encoders 18.1, 18.2. In addition, it has a front panel window 24 through which the display is visible from the outside.

The front panel 21 is bolted to the printed-circuit board 15 at the corners of the front panel window 24 by means of bolts 25 where sleeves 26 define the distance from the printed-circuit board 15.

The control device 4.1 further comprises the operator interface 6.1 which comprises an operator interface bottom portion 27 made of a relatively rigid material and a membrane 28.1 at the outside. The operator interface bottom portion 27 has a circumferential edge 29 which can be snap-fitted into an edge 30 of the casing bottom portion 5.

The operator interface bottom portion 27 further has a multiplicity of holes 31.1 to 31.4 which are associated with the push-button switches 16.1 to 16.4. The push-button switches 16.1 to 16.4 plunge into the corresponding holes 31.1 to 31.4 or are oriented thereto. The operator interface bottom portion 27 further has holes 32.1, 32.2 which are oriented to the angle encoders 18.1, 18.2.

The membrane 28.1 has surface areas 33.1 to 33.4 which are associated with the push-button switches 16.1 to 16.4. The membrane 28.1 is adhered to an outside of the operator interface bottom portion 27. Here, the marked interfacial areas 33.1 to 33.4 are precisely associated with the holes 31.1 to 31.4 which are oriented to the relative push-button switches 16.1 to 16.4 in the operator interface bottom portion 27 when the operator interface bottom portion 27 has been snap-fitted into the casing bottom portion 5.

The inside of the operator interface bottom portion 27 accommodates the perforated mask 34 which has holes 35.1, 35.2 which is associated with the angle encoders 18.1, 18.2. The mask further has holes 35.2 which receive the buttons of the push-button switches 16.2. Finally, it has holes 35.3 which are oriented to the push-button switches 16.3.

Adapter buttons 36 which have an annular disc shaped protrusion 37 at the circumference are arranged between the perforated mask 34 and the inside of the operator interface bottom portion 27. The adapter buttons 36 engage the holes 31.3 of the operator interface bottom portion 27, on one hand, and the holes 35.3, on the other where they are secured by the protrusion 37 between the perforated mask 34 and the operator interface bottom portion 27. The adapter buttons 36 abut against the inside of the flexible membrane below the surface areas 33.3, on one hand, and the push-button switches 16.3, on the other when the operator interface 6.1 has been snap-fitted into the casing bottom 5. The push-button switches 16.1, 16.2, and 16.4 will then abut against the insides of the surfaces of the elements 33.1, 33.2, 33.4.

The display 10 is visible from the outside through a further window 38 in the operator interface bottom portion 27 and a frame 39 in the transparent membrane 28.1.

The operator interface 6.1 has a surface which substantially is smooth and liquid-tight.

Pressing the surface areas 33.1 to 33.4 which define press keys enables an actuation of the push-button switches 16.1 to 16.4. The angle encoders 18.1, 18.2 have no function on this operator interface 6.1. The display 10 is visible within the frame 39.

Figure 4:
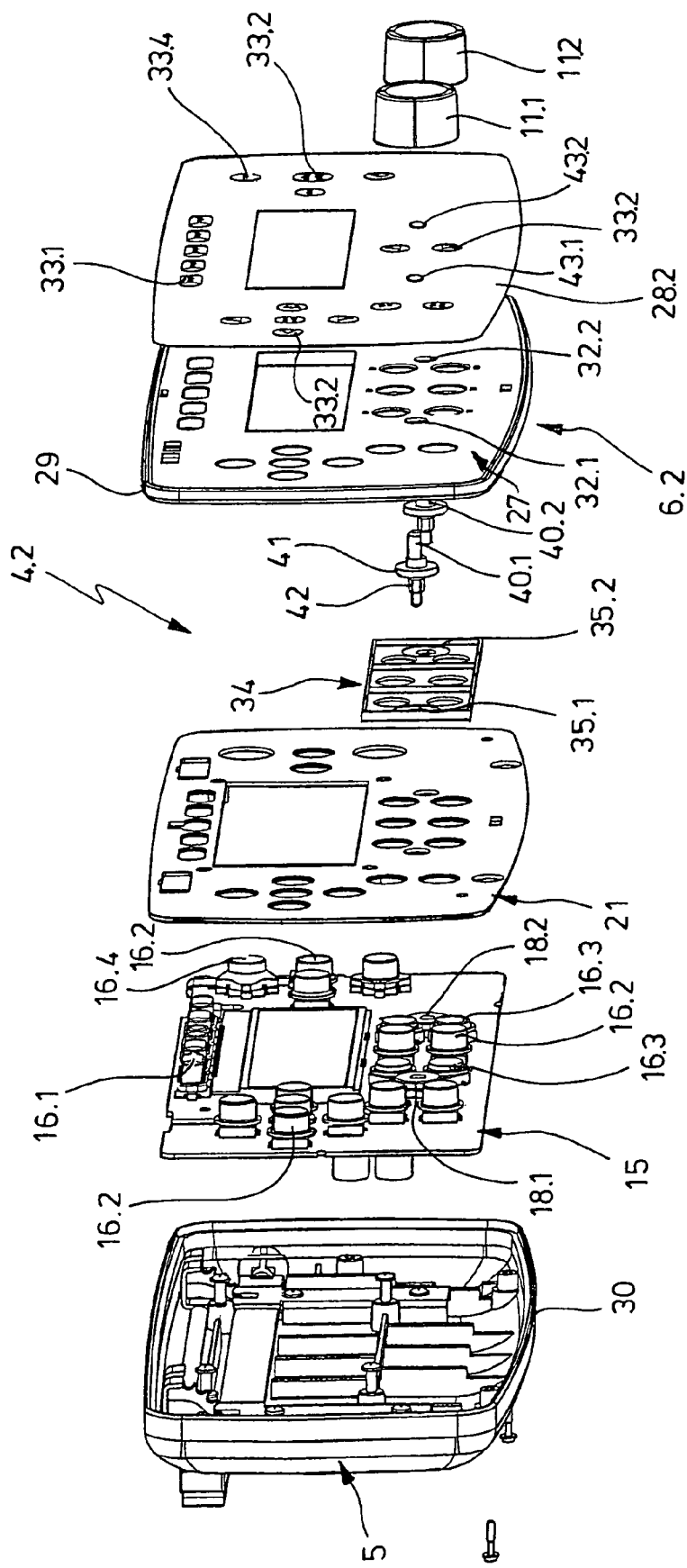
FIG. 4 the control device of the same laboratory centrifuge with an operator interface having keys and rotary knobs in an exploded perspective view.

In FIG. 4, the control device 4.2 has the same bottom casing portion 5, the same printed-circuit board 15, the same front panel 21, the same perforated mask 34, and the same operator interface bottom portion 27 as has the control device 4.1.

Between the operator interface bottom portion 27 and the perforated mask 34, the operator interface 6.2 has two axes 40.1, 40.2 which circumferentially carry an annular disc 41 and externally carry a hexagon 42 in the vicinity of an end. The axes 40.1, 40.2 are passed through holes 35.1, 35.2 of the perforated mask 28.2 and through the holes 32.1, 32.2 of the operator interface bottom portion 27 in the completely assembled operator surface 6.2. The annular discs 41 hold the axles 40.1, 40.2 in place between the perforated mask 28.2 and operator interface bottom portion 27.

The operator interface 6.2 further has a flexible membrane 28.2 which differs from the membrane 28.1 of FIG. 3 in that it has two membrane holes 43.1, 43.2 in place of the surface areas 33.3. The membrane 28.2 is adhered to the outside of the operator interface bottom portion 27. The membrane holes 43.1, 43.2 are oriented to the holes 32.1, 32.2 here. The axes 40.1, 40.2 are passed through the holes 32.1, 32.2, and 43.1, 43.2. At the outside, the rotary knobs 11.1, 11.2 are pressed onto the axes 40.1, 40.2.

Snap-fitting the operator interface 6.2 together with the casing bottom portion 5, in turn, allows the push-button switches 16.1, 16.2, and 16.4 to be brought to abut against the corresponding interfacial areas 33.1, 32.2 and 33.4 of the membrane 28.2. Since there are no adapter buttons 36 a mechanical contact is not established between the push-button switches 16.3 and membrane 28.2. However, the axes 40.1, 40.2 are introduced into corresponding holes of the angle encoders 18.1, 18.2 which are designed as being complementary to the hexagon 42 so that a connection fixed for rotation will result.

In this way, the laboratory centrifuge 1 can be equipped with a substantially smooth membrane keyboard 7.1 with membrane keys 8.3, 8.5 for an adjustment of the centrifugation time and number of revolutions, on one hand, and an operator interface 6.2 with a membrane keyboard 7.2 and rotary knobs 11.1, 11.2 for an adjustment of the centrifugation time and number of revolutions, on the other. The user is able to readily exchange the operator interfaces 6.1, 6.2 and, hence, equip the control device the way he desires. For example, the laboratory centrifuge will be delivered with only one operator interface 6.1 or 6.2 and the other operator interface 6.2 or 6.1 will be delivered later in case of need or will be exchanged. It is also possible to deliver the laboratory centrifuge with the two operator interfaces 6.1, 6.2 from the very beginning so that the user may employ the operator interface of his choice at any time.

The pivoting holder 11 allows to pivot the control device 4.1, 4.2 to a pivoted position as desired by the user and the detenting device 13 enables it to be locked in the position concerned. The locked condition may be cancelled by an actuation of the unlocking button 14.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:

1. A laboratory apparatus having at least one control device disposed on an instrument body of the laboratory apparatus, the at least one control device comprising:
    an electric printed circuit board with at least two control elements, one of the control elements being a push-button switch and one of the control elements being an angle encoder;
    a first operator interface and a second operator interface different from the first operator interface, wherein the second operator interface is interchangeable with the first operator interface, wherein each operator interface includes at least one operator control selected from the group consisting of touch-sensitive membrane keys, press keys and rotary knobs;
    a retaining device for detachably holding either one of the first and second operator interfaces on the instrument body with the at least one operator control of the operator interface oriented to one of the control elements of the electric printed circuit board; and
    a mechanical and/or magnetic connection for detachably joining at least one of the control elements to the operator control.

2. The laboratory apparatus according to claim 1, further comprising: an electric connection between the control device and the instrument body for releasably joining the control device to the instrument body.

3. The laboratory apparatus according to claim 1, wherein one of the operator interfaces is a substantially flat interface with at least one press key.

4. The laboratory apparatus according to claim 1, wherein all of the operator controls of the control device are touch-sensitive membrane keys.

5. The laboratory apparatus according to claim 1 wherein one of the operator interfaces has at least one flexible interfacial element which, when the operator interface is held on the instrument body, has an inside abutted directly, or via an adapter button indirectly, to the front face of a push-button switch disposed on the electric printed circuit board.

6. The laboratory apparatus according to claim 5 wherein one of the operator interfaces comprises a rigid bottom portion with at least one hole partially accommodating the front face of the push-button switch or the adapter button; and a membrane disposed at an outside of the rigid bottom portion.

7. The laboratory apparatus according to claim 6 wherein at least one adapter button plunges into a hole of the rigid bottom portion and into a hole of a perforated mask and has a circumferentially-sided protrusion which is arranged to be axially arranged between the rigid bottom portion and at least one perforated mask attached to the rigid bottom portion.

8. The laboratory apparatus according to claim 1, wherein all of the control elements of the first operator interface are touch-sensitive memory keys and the second operator interface has at least one operator control that is a rotary knob and at least one of the control elements is an angle encoder; wherein an axis of rotation is joined to the rotary knob penetrates through the operator interface, the angle encoder is joined to the axis of rotation and disposed on the electric printed circuit board, and the rotary knob is rotatably connected to the angle encoder.

9. The laboratory apparatus according to claim 8 wherein the axis of rotation penetrates through a hole of at least one perforated mask attached to a rigid bottom portion of the operator interface, and the axis of rotation has an annular disk disposed between the rigid bottom portion and the at least one perforated mask (34).

10. The laboratory apparatus according to claim 8 wherein the axis of rotation has a snap-fit connection fixed for rotation with the angle encoder.

11. The laboratory apparatus according to claim 1 wherein a display of a display device is visible in a window of the control device.

12. The laboratory apparatus according to claim 11 wherein the electric printed-circuit board carries a display device and one of the operator interfaces has the window.

13. The laboratory apparatus according to claim 1 wherein the control device has a casing bottom portion disposed on the instrument body in which the electric printed circuit board is held and which has the retaining device for detachably holding the operator interface on the casing bottom portion.

14. The laboratory apparatus according to claim 13 wherein a pivoting holder for pivotably holding the casing bottom portion on the instrument body exists between the casing bottom portion and instrument body.

15. The laboratory apparatus according to claim 14 wherein a detenting device for the casing bottom portion in different pivoting positions with respect to the instrument body exists between the casing bottom portion and instrument body.

16. A laboratory apparatus of claim 1, wherein the at least one operator control of the first operator interface comprises at least a pair of keys, wherein one key serves to increase a setting and the other key serves to decrease the same setting, and the at least one operator control of the second operator interface comprises a rotary knob for adjustment of the same setting.

17. The laboratory apparatus according to claim 16 wherein the rotary knob or an axis connected thereto at least partially penetrates through a hole in an operator interface, and a stopper adapted to be forced into the hole when the rotary knob is detached from the angle encoder (18).

18. The laboratory apparatus according to claim 1 which has a locking device which prevents the operator interface or control device or rotary knob from becoming loose when a centrifuge is turned on or a certain centrifuge function is activated.

19. The laboratory apparatus according to claim 1 which is a laboratory centrifuge or sample preparation apparatus.

* * * * *